(12) United States Patent
Wang et al.

(10) Patent No.: US 11,129,867 B2
(45) Date of Patent: Sep. 28, 2021

(54) METHOD OF TREATING CANCER CELLS

(71) Applicant: NATIONAL TSING HUA UNIVERSITY, Hsinchu (TW)

(72) Inventors: Hui-Ching Wang, Hsinchu (TW); Dah-Tsyr Chang, Hsinchu (TW); Yu-Hsuen Tu, Hsinchu (TW); Ping-Hsueh Kuo, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 0 days.

(21) Appl. No.: 16/264,702

(22) Filed: Feb. 1, 2019

(65) Prior Publication Data
US 2019/0151402 A1  May 23, 2019

Related U.S. Application Data

(60) Provisional application No. 62/576,050, filed on Oct. 23, 2017.

(51) Int. Cl.
| | |
|---|---|
| *A61K 38/04* | (2006.01) |
| *A61K 38/08* | (2019.01) |
| *A61K 47/64* | (2017.01) |
| *A63F 13/67* | (2014.01) |
| *A63F 13/60* | (2014.01) |
| *A61K 47/54* | (2017.01) |
| *A61P 35/00* | (2006.01) |
| *A61K 31/352* | (2006.01) |
| *A61K 41/00* | (2020.01) |
| *G06N 3/12* | (2006.01) |
| *G06T 1/20* | (2006.01) |

(52) U.S. Cl.
CPC ............ *A61K 38/08* (2013.01); *A61K 31/352* (2013.01); *A61K 41/0057* (2013.01); *A61K 47/545* (2017.08); *A61K 47/64* (2017.08); *A61P 35/00* (2018.01); *A63F 13/60* (2014.09); *A63F 13/67* (2014.09); *G06N 3/126* (2013.01); *G06T 1/20* (2013.01); *A63F 2300/60* (2013.01)

(58) Field of Classification Search
None
See application file for complete search history.

(56) References Cited

PUBLICATIONS

Srinivasan, PLoS One 6(3), 2011, pp. 1-10 (Year: 2011).*
Fang, PLoS One 8(3), 2013, pp. 1-10 (Year: 2013).*
Website: https://www.thermofisher.com/us/en/home/life-science/cell-analysis/fluorophores/fluorescein.html, retrieved on Oct. 10, 2019, 3 pages (Year: 2019).*
Website: https://www.google.com/search?ei=gxCfXe_tLOe0ggeLs4vwCQ&q=squamous+cells+de, retrieved on Oct. 11, 2019, 2 pages. (Year: 2019).*
Cortese, Mayo Clinic Proceedings; Jul. 1997; 72, 7; ProQuest p. 595 (Year: 1997).*
T. Gambichler et al., Narrowband UVB phototherapy in skin conditions beyond psoriasis, J AM Acad Dermatol vol. 52, No. 4, pp. 660-670, Apr. 2005.
S. Paus et al., Bright Light Therapy in Parkinson's Disease: A Pilot Study, Movement Disorders, vol. 22, No. 10, pp. 1495-1498, May 2007.
D. Srinivasan et al., Conjugation to the Cell-Penetrating Peptide TAT Potentiates the Photodynamic Effect of Carboxytetramethylrhodamine, PLoS One, vol. 6, Issue 3, e17732, Mar. 2011.
T. Fan et al., Characterization of Molecular Interactions between Eosinophil Cationic Protein and Heparin, The Journal of Biological Chemistry, vol. 283, No. 37, pp. 25468-25474, Sep. 12, 2008.
S. Fang et al., A Novel Cell-Penetrating Peptide Derived from Human Eosinophil Cationic Protein, PLOS One, vol. 8, Issue 3, e57318, Mar. 2013.
L. V. Johnson et al., Localization of mitochondria in living cells with rhodamine 123, Froc. Natl. Acad. Sc. USA vol. 77, No. 2, pp. 990-994, Feb. 1980.
A. Canitano et al., Proton pump inhibitors induce a caspase-independent antitumor effect against human multiple myeloma, multiple myeloma, Cancer Letters (2016), doi: 10.1016/j.canlet.2016.04.015.
M. Kurita et al., Indirubin 3'-Epoxide Induces Caspase-Independent Cell Death in Human Neuroblastoma, Biol. Pharm. Bull. vol. 39, No. 6, pp. 993-999 (Mar. 2016).
T. Ogura et al., Docetaxel induces Bcl-2- and pro-apoptotic caspase-independent death of human prostate cancer DU145 cells, International Journal of Oncology 48: 2330-2338, Mar. 2016, DOI: 10.3892/ijo.2016.3482.
K. A. Sarosiek et al., Directly targeting the mitochondrial pathway of apoptosis for cancer therapy using BH3 mimetics—recent successes, current challenges and future promise, The FEBS Journal 283, 3523-3533, Mar. 2016, doi:10.1111/febs.13714.
M. Oba et al., A Cell-Penetrating Peptide with a Guanidinylethyl Amine Structure Directed to Gene Delivery, Scientific Reports | 6:19913 | DOI: 10.1038/srep19913, 2016.
Kiran H. Lagisetty et al., Squamous cell carcinomas and adenocarcinomas of the esophagus: One treatment does not rule them all, The Journal of Thoracic and Cardiovascular Surgery, Oct. 2017, vol. 154, No. 4, pp. 1446-1447.

* cited by examiner

*Primary Examiner* — Satyanarayana R Gudibande
(74) *Attorney, Agent, or Firm* — Demian K. Jackson; Jackson IPG PLLC

(57) ABSTRACT

The present invention discloses a method of treating cancer cells. The method comprises administrating a composition comprises a rhodamine or rhodamine derivative conjugated to a peptide comprises an amino acid sequence of SEQ ID NO: 1 to a subject in need, and activate the composition with light.

10 Claims, 11 Drawing Sheets
(2 of 11 Drawing Sheet(s) Filed in Color)
Specification includes a Sequence Listing.

METHOD OF TREATING CANCER CELLS

This application contains a Sequence Listing in computer readable form. The computer readable form is incorporated herein by reference in its entirety.

FIELD OF THE INVENTION

This invention is about a method of treating cancer cells, comprising: administrating a composition comprises a rhodamine or rhodamine derivative conjugated to a peptide comprises the sequence of SEQ ID NO: 1 to a subject in need, and activate the composition with light.

BACKGROUND OF THE INVENTION

Current Status and Therapy of Oral Cancer

Oral cancer is one of the 10 most frequent cancers worldwide, with an estimated incidence of over 500,000 new cases diagnosed annually. About 95% of oral cancer is oral squamous cell carcinoma (OSCC) and can occur anywhere in the oral cavity, including tongue, lips, gingiva, buccal mucosa and palate. It could also spread locally to perioral structures or metastasize to regional and distant lymph nodes.

Oral cancer is one of the ten most common cancers in the world. Delayed clinical detection, poor prognosis, and the absence of specific biomarkers challenge effective treatment options and expensive therapeutic alternatives. To date, there are only limited treatment options available for oral cancer. The major treatment strategies for OSCC are surgery, radiotherapy, and chemotherapy including docetaxel, 5-fluorouracil, cisplatin, or could combined with cetuximab, one targeted therapy approved as another new treatment option. However, the fear of side effects of treatment, disFigurement, and being in pain are the major clinical obstacles for the implementation of treatment. Present studies are focused on discovery and development of novel therapies for oral cancer, that necessary to control the ever rising oral cancer related mortalities. Targeted therapy for oral cancer is still a relatively new concept, and more studies are needed to confirm the clinical effectiveness of the drugs for chemotherapy. Phototherapy employs either UV or visible light, with or without a photosensitizer, a molecule capable of absorbing light energy and transferring that energy to adjacent molecules (Gambichler, T., Breuckmann, F., Boms, S., Altmeyer, P., and Kreuter, A. (2005). Narrowband UVB phototherapy in skin conditions beyond psoriasis. Journal of the American Academy of Dermatology 52, 660-670; Paus, S., Schmitz-Hubsch, T., Wullner, U., Vogel, A., Klockgether, T., and Abele, M. (2007). Bright light therapy in Parkinson's disease: a pilot study. Movement disorders: official journal of the Movement Disorder Society 22, 1495-1498; Srinivasan, D., Muthukrishnan, N., Johnson, G. A., Erazo-Oliveras, A., Lim, J., Simanek, E. E., and Pellois, J. P. (2011). Conjugation to the cell-penetrating peptide TAT potentiates the photodynamic effect of carboxytetramethylrhodamine. PloS one 6, e17732). It is used clinically to treat malignant cancers including head and neck, lung, bladder and particular skin. While with relatively few side effects, medicines for phototherapy especially on squamous cell carcinoma such as oral cancer are limit. This further highlights the importance of developing early diagnosis and early treating methods.

Heparan sulfate proteoglycans (HSPGs) are glycoproteins with one or more covalently attached heparan sulfate (HS) chains, a type of glycosaminoglycan (GAG). HSPG are found on the cell surface or in the extracellular matrix, where they interact with a plethora of ligands. The role of HSPG as a cell-surface receptor of diverse macromolecular cargo has recently been manifested. Exosomes, cell penetrating peptides, polycation-nucleic acid complexes, viruses, lipoproteins, growth factors and morphogens among other ligands enter cells through HSPG-mediated endocytosis. HSPG can be classified into three groups according to their subcellular locations: membrane HSPG, such as syndecans and glypicans; the secreted extracellular matrix HSPG (type XVIII collagen, perlecan); and the secretory vesicle proteoglycans (serglycin). In addition, HSPGs can bind growth factors, chemokines, cytokines, and morphogens, protecting them against proteolysis. These interactions provide a depot of regulatory factors that can be liberated by selective degradation of the HS chains. The past studies had also reported that cell surface HSPGs facilitate the formation and signaling of FGF2-FGF receptor complexes.

GAG-Binding Peptide

GAG-binding peptide is a peptide derived from eosinophil cationic protein (ECP), which is secreted by eosinophil. The eosinophil, a granulated blood cell, is a multifunctional leukocyte associated with inflammatory processes such as parasitic infections, asthma, and allergic diseases. In response to different stimuli, eosinophils are recruited to inflammatory area and secrete granular proteins, including major basic proteins (MBP), eosinophil peroxidase (EPO), eosinophil cationic protein (ECP), eosinophil-derived neurotoxin (EDN), and lipid mediators. ECP, classified as human RNase3, is released from activated eosinophils to promote eliminating the invading microbs. Besides eliminating invading microbes, ECP has multifunctional properties such as ribonucleolytic, cytotoxic, anti-virus and heparan binding activities.

Moleculer interaction between ECP and heparan has been characterized and heparan binding motif in ECP was identified (Fan, T. C., Chang, H. T., Chen, I. W., Wang, H. Y, and Chang, M. D. (2007). A heparan sulfate-facilitated and raft-dependent macropinocytosis of eosinophil cationic protein. Traffic 8, 1778-1795). A specific sequence of ECP, $^{34}$RWRCK$^{38}$, has been identified as a heparan-binding motif (Fan, T. C., Fang, S. L., Hwang, C. S., Hsu, C. Y., Lu, X. A., Hung, S. C., Lin, S. C., and Chang, M. D. (2008). Characterization of molecular interactions between eosinophil cationic protein and heparin. The Journal of biological chemistry 283, 25468-25474). Specifically 10-residue peptide, $^{32}$NYRWRCKNQN$^{41}$ (SEQ ID NO. 2), is identified as a cell-penetrating peptide (represented in GBP in the following paragraphs) derived from the heparin binding motif of ECP. GBP has been shown that possesses heparan sulfate binding and cell penetrating activities (Fan, T. C., Fang, S. L., Hwang, C. S., Hsu, C. Y, Lu, X. A., Hung, S. C., Lin, S. C., and Chang, M. D. (2008). Characterization of molecular interactions between eosinophil cationic protein and heparin. The Journal of biological chemistry 283, 25468-25474; Fang, S. L., Fan, T. C., Fu, H. W., Chen, C. J., Hwang, C. S., Hung, T. J., Lin, L. Y, and Chang, M. D. (2013). A novel cell-penetrating peptide derived from human eosinophil cationic protein. PloS one 8, e57318). Notably, GBP is able to deliver a small fluorescent molecule, a recombinant protein, nanoparticles, and a peptidomimetic drug into cells (Fang, S. L., Fan, T. C., Fu, H. W., Chen, C. J., Hwang, C. S., Hung, T. J., Lin, L. Y, and Chang, M. D. (2013). A novel cell-penetrating peptide derived from human eosinophil cationic protein. PloS one 8, e57318). Taken together, GBP possesses prominent clinical implications for drug delivery.

Rhodamine and Rhodamine Derivatives

Rhodamine is a family of related chemical compounds, fluorone dyes. They are usually used as a tracer to observe the rate and direction of flow and transport. Rhodamine dyes are generally toxic, and are soluble in water, methanol and ethanol. There are many rhodamine derivatives used for imaging purposes, including Carboxytetramethylrhodamine (TAMRA), Tetramethylrhodamine (TMR) and 5/6-tetramethyl-rhodamine isothiocyanate (TRITC). TMR, one of the rhodamine derivatives, has been used extensively in protein, oligonucleotide labelling, and DNA sequencing, amongst other areas. The past study had reported that rhodamine 123, a mitochondrial-specific fluorescent dye, been used previously to specifically localize mitochondria in living cells (Johnson, L. V., Walsh, M. L., and Chen, L. B. (1980). Localization of mitochondria in living cells with rhodamine 123. Proceedings of the National Academy of Sciences of the United States of America 77, 990-994).

Mechanisms of Cell Death

Apoptosis is an evolutionarily conserved biological process of cell suicide program that is required for normal development and homeostasis of multicellular organism, and is also implicated in many pathological processes. Apoptosis is characterized by marked morphological alterations of cells, such as membrane blebbing, DNA degradation, nuclear fragmentation, chromatin condensation, and cleavage of some cellular proteins, such as Poly (ADP-ribose) polymerase (PARP). Apoptosis is usually induced through two distinct signaling pathways, including the mitochondrial pathway and the death receptor pathway. The mitochondrial pathway usually involves the release of mitochondrial cytochrome c to the cytosol. Moreover, the Bcl-2 family members are known to play important roles in controlling the release of cytochrome c from mitochondria. Upon apoptotic signals, pro-apoptotic Bcl-2 members, such as Bax, Bak or Bid, are activated. In contrast, anti-apoptotic members including Bcl-2 and Bcl-XL can prevent this occurrence.

PARP is a family of proteins involved in a number of cellular processes such as DNA repair, genomic stability, and programmed cell death. PARP can be selectively cleaved by caspase during apoptosis and become incapable of responding to DNA damage. It was generally believed that PARP cleavage was catalyzed by caspase-3, but PARP cleavage by caspase-7 has also been reported. Although PARP is one of the potential target molecules of caspases, the cleavage has been regarded as an evidence of caspase activation and has been widely used as a hallmark of cell apoptosis. Nonetheless, in recent years, it has been shown that PARP cleavage can be detected in the absence of procaspase-3 or -7 cleavage, and thus could be independent of activation of caspase-3 or -7. Many previous studies have investigated alternative killing of tumor cells through a mitochondrial route involving caspase-independent apoptotic signaling (Canitano, A., Iessi, E., Spugnini, E. P., Federici, C., and Fais, S. (2016). Proton pump inhibitors induce a caspase-independent antitumor effect against human multiple myeloma. Cancer letters 376, 278-283; Kurita, M., Hanada, S., Ichimaru, Y, Saito, H., Tabata, K., Asami, S., Miyairi, S., and Suzuki, T. (2016). Indirubin 3'-Epoxide Induces Caspase-Independent Cell Death in Human Neuroblastoma. Biological & pharmaceutical bulletin 39, 993-999; Ogura, T., Tanaka, Y, Tamaki, H., and Harada, M. (2016). Docetaxel induces Bcl-2- and pro-apoptotic caspase-independent death of human prostate cancer DU145 cells. International journal of oncology 48, 2330-2338; Sarosiek, K. A., and Letai, A. (2016). Directly targeting the mitochondrial pathway of apoptosis for cancer therapy using BH3 mimetics—recent successes, current challenges and future promise. The FEBS journal 283, 3523-3533). In addition to release of cytochrome-c, mitochondrial outer membrane permeabilization results in the release of various proteins in response to organelle damage. Based on these evidence, understanding of caspase-independent apoptosis could provide new opportunities for the development of novel, efficacious cancer therapies.

Reactive Oxygen Species (ROS) in Cancer

ROS are chemically reactive chemical species containing oxygen, such as peroxides, superoxide, hydroxyl radical, and singlet oxygen. In a biological context, ROS are formed as a natural byproduct of the normal metabolism of oxygen and have important roles in cell signaling and homeostasis. However, during times of environmental stress (e.g., UV or heat exposure), ROS levels can increase dramatically. Elevated rates of ROS have been detected in almost all cancers, where they promote many aspects of tumor development and progression. High levels of ROS in cancer cells can result from increased metabolic activity, peroxisome activity, mitochondrial dysfunction, increased activity of oxidases, or through crosstalk with infiltrating immune cells. Clinically, ROS production is a mechanism shared by all non-surgical therapeutic approaches for cancers, including radiotherapy, chemotherapy and photodynamic therapy, due to their implication in triggering cell death, thus ROS are also used to kill cancer cells. Countless studies have documented that sustained or constitutive production of ROS in cancer cells is inversely correlated with apoptotic cell death. Increased ROS generation or decreased ROS scavenging capacity plays a crucial role in cell physiology. Excessive cellular ROS amounts can cause oxidative damage to various cells, leading to apoptosis and cell death. Therefore, some cancer cells are more sensitive to oxidative stress induced by exogenous ROS-generating compounds that increase intracellular ROS levels. To date, a number of natural agents targeting accumulation of ROS have attracted significant interest and have led to clinical trials and therapies.

N-acetylcysteine (NAC)

NAC is the acetylated variant of the amino acid L-cysteine and is widely used as the specific antidote for acetaminophen overdose. NAC, as a safe and inexpensive nutritional supplement or medication, is commercially accessible since long-time ago. NAC acts directly as a scavenger of free radicals, especially oxygen radicals. It is also recommended as a potential treatment option for different disorders resulted from generation of free oxygen radicals. Thus, NAC is considered an important antioxidant. The abundant of glutathione (GSH) plays an important role in the regulation of apoptosis due to its role as a substrate of ROS scavenging enzymes. Therefore, NAC has been widely used as a research tool in the field of apoptosis research for investigating the role of ROS in induction of apoptosis.

Furthermore, NAC is a well-tolerated mucolytic drug that moderates clinging mucous secretions and enhances glutathione S-transferase activity. To date, NAC has applied in treatment of several diseases, such as liver cancer, polycystic ovary syndrome, chronic bronchitis, asthma, Alzheimer disease, Parkinson disease, and so on. As a drug, NAC represents perhaps the ideal xenobiotic, capable of directly entering endogenous biochemical processes as a result of its own metabolism. The more understood about the actions of NAC, the clinical applications have also broadened. NAC is now widely used as a mucolytic and in the treatment of human immunodeficiency virus HIV, and it has reported efficacy in chronic obstructive pulmonary disease and contrast-induced nephropathy.

SUMMARY OF THE INVENTION

This invention is about a method of treating cancer cells, comprising: administrating a composition comprises a rhodamine or rhodamine derivative conjugated to a peptide comprises the sequence of SEQ ID NO: 1 to a subject in need, and activate the composition with light.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
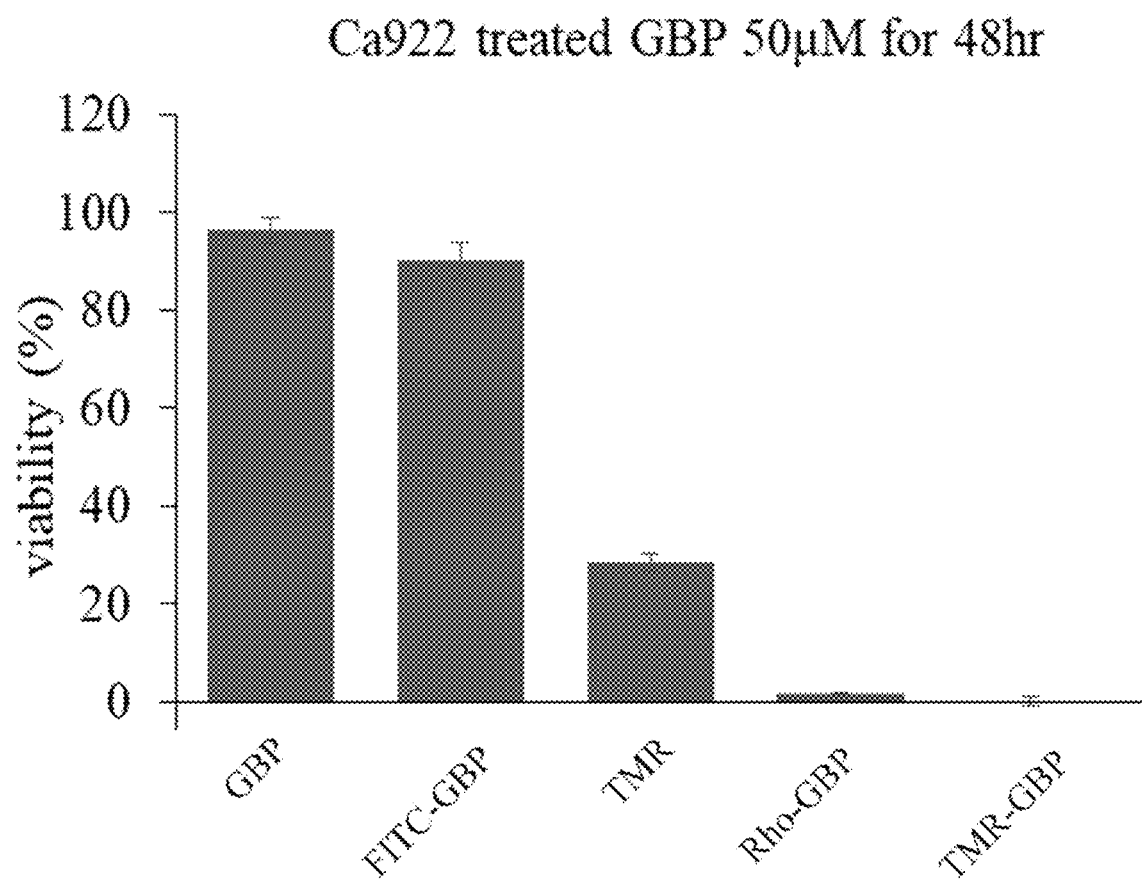
FIG. 1 shows that conjugation to rhodamine and TMR induce GBP cytotoxicity. To investigate the effect of different GBP on oral cancer, Ca922 cells were treated with indicated GBP 50 μM for 48 hours and measured cells viability by WST-8 assay.

This invention aims to explore the role of a specific tetramethylrhodamine (TMR)-conjugated GAG-binding peptide (TMR-GBP, which represents in TMR-GBP in abstract) on regulating cancer cell motility.

This invention discloses that TMR-GBP induced cytotoxicity in specific cell lines. To understand the nature of cytotoxicity induced by TMR-GBP, cells were treated with the peptide or peptide conjugated with different chemicals, among which TMR-GBP and its analog induced significant cytotoxic effect on the specific cell lines. Notably, it was found that TMR-GBP induced PARP cleavage in the absence of caspase activity. In addition, mitochondria fragmentation and cytochrome-c release were detected in the presence of TMR-GBP. It was also found that TMR-GBP induced cytotoxicity was independent of calcium release. Conversely, TMR-GBP-induced cytotoxicity was diminished upon the treatment with anti-oxidant reagent. In conclusion, TMR-GBP induces caspase-independent cell death, which is mediated by mitochondria fragmentation, cytochrome-c release, PARP cleavage, and ultimately leading to apoptosis in specific cell lines.

In this invention, it is found that TMR-GBP treatment induced production of intracellular ROS. ROS accumulate as a result of dysfunction in the mitochondrial respiratory chain. Therefore, according to the data of immunofluorescence staining presented, mitochondria fragmentation and cytochrome-c release were detected in the presence of TMR-GBP. Moreover, release of cytochrome-c from mitochondria is a major event during apoptosis. Cytochrome-c was also found to induce chromatin condensation. In this invention, it is also detected that TMR-GBP induced DNA damage and PRRP cleavage, leading to oral cancer cells apoptosis.

In this invention, TMR-GBP inhibited cell viability in various oral cancer cells. Interestingly, the cell viability was not markedly affected in breast cancer, embryonic kidney, cervical cancer, liver cancer and lung cancers. Furthermore, the most oral cancer cells used in this invention were squamous carcinoma, and other types were epithelial-origin. Thus, GBP-mediated cytotoxicity restricts to squamous carcinoma.

In this invention, it is found that TMR-GBP induced cytotoxicity was partially suppressed by NAC. In this invention, both DNA damage and ROS production were reversed by NAC treatment in the presence of TMR-GBP. Thus, NAC could promote cell viability upon TMR-GBP on oral cancer cells. Notably, the clinical applications of NAC have broadened currently, and some people also use NAC as a dietary supplement. However, according to this invention, it is not recommended that oral cancer patient simultaneously intake any supplement containing NAC upon TMR-GBP or chemotherapy drug treatments which will inhibit cytotoxicity of TMR-GBP.

In this invention, an unexpected cytotoxic role of TMR-GBP specifically on oral cancer cells is discovered. Because chemotherapy and radiation therapy have many side effects and inconvenience, TMR-GBP could be considered applicable for the development of ointment for patient convenience. Moreover, according to this invention, it is found that TMR-GBP induced cytotoxicity is light-sensitive. Thus, treatment can be improved by light stimulation.

Accordingly, this invention is about a method of treating cancer cells, comprising: administrating a composition comprises a rhodamine or rhodamine derivative conjugated to a peptide comprises an amino acid sequence of SEQ ID NO: 1 to a subject in need, and activate the composition with light.

SEQ ID NO:1 is presented by the following sequence:
Asn Tyr Arg Xaa Arg Cys Lys Asn Gln Asn In one embodiment, the Xaa at position 4 of SEQ ID NO: 1 represents Trp or Arg. For example, the peptide variant can comprise SEQ ID NO:2 or SEQ ID NO: 3.

SEQ ID NO:2 is presented by the following sequence:
Asn Tyr Arg Trp Arg Cys Lys Asn Gln Asn SEQ ID NO:3 is presented by the following sequence:
Asn Tyr Arg Arg Arg Cys Lys Asn Gln Asn In one embodiment, the composition is administrated into a mass of cancer cells.

In one embodiment, the composition is administrated by enteral administration.

In one embodiment, the composition is administrated by infusion into a mass of cancer cells.

In one embodiment, said composition is administrated by injection into a mass of proliferating cells.

In one embodiment, said composition is administrated into a resection cavity or scar.

In one embodiment, the cancer cells are carcinoma cells. In another embodiment, the carcinoma cells are squamous cell carcinoma cells.

In one embodiment, the cancer cells are derived from cells of upper aerodigestive tract.

In one embodiment, the composition induces apoptosis of the cancer cells. In another embodiment, the apoptosis is independent of caspase activation.

In one embodiment, the composition induces mitochondria fragmentation of the cancer cells.

In one embodiment, the composition induces ROS generation of the cancer cells.

In one embodiment, the composition induces DNA damage of the cancer cells.

In one embodiment, the light is with a wavelength of 380 nm to 750 nm.

In one embodiment, the light is with a wavelength of 400 nm to 620 nm.

In one embodiment, the light is with a wavelength of 470 nm to 580 nm.

This invention is also about a composition for treating cancer cells, comprising: a rhodamine or rhodamine derivative, and a peptide comprises the sequence of SEQ ID NO: 1, wherein the rhodamine or rhodamine derivative is conjugated to the peptide.

SEQ ID NO:1 is presented by the following sequence:
Asn Tyr Arg Xaa Arg Cys Lys Asn Gln Asn In one embodiment, the Xaa at position 4 of SEQ ID NO: 1 represents Trp or Arg. For example, the peptide variant can comprise SEQ ID NO:2 or SEQ ID NO: 3.

SEQ ID NO:2 is presented by the following sequence:
Asn Tyr Arg Trp Arg Cys Lys Asn Gln Asn SEQ ID NO:3 is presented by the following sequence:
Asn Tyr Arg Arg Arg Cys Lys Asn Gln Asn In one embodiment, the cancer cells are carcinoma cells. In another embodiment, the carcinoma cells are squamous cell carcinoma cells.

In one embodiment, the cancer cells are derived from cells of upper aerodigestive tract.

In one embodiment, the composition induces apoptosis of the cancer cells. In another embodiment, the apoptosis is independent of caspase activation.

In one embodiment, the composition induces mitochondria fragmentation of the cancer cells.

In one embodiment, the composition induces ROS generation of the cancer cells.

In one embodiment, the composition induces DNA damage of the cancer cells.

In one embodiment, the composition is activated with light.

In one embodiment, the light is with a wavelength of 380 nm to 750 nm.

In one embodiment, the light is with a wavelength of 400 nm to 620 nm.

In one embodiment, the light is with a wavelength of 470 nm to 580 nm.

As used herein, the term "cancer" is meant to be interpreted in the broadest sense, and to include solid and nonsolid malignancies, premalignancies, and tumors which are malignant by virtue of their location.

As used herein, the term "squamous cell carcinoma" includes, but not limits to, head and neck squamous cell carcinoma, squamous cell thyroid carcinoma, esophageal cancer, squamous cell carcinoma of the lung, squamous cell carcinoma of the penis such as Bowen's disease, Erythoroplasia of Quetrat, and Bowenoid papulosis, squamous cell carcinoma of the prostate, vagina squamous cell carcinoma, and bladder cancer.

As used herein, the term "subject" refers to any living organism which can be administered to the pharmaceutical compositions of the present invention and in which cancer or a proliferative disorder can occur. The term includes, but is not limited to, humans, non-human animals, for example non-human primates such as chimpanzees and other apes and monkey species; farm animals such as cattle, sheep, pigs, goats and horses, domestic subjects such as dogs and cats, laboratory animals including rodents such as mice, rats and guinea pigs, and the like. The term does not denote a particular age or sex. Thus, adult and newborn subjects, as well as fetuses, whether male or female, are intended to be covered. The term "subject" also includes living organisms susceptible to conditions or disease states as generally disclosed, but not limited to, throughout this specification. Examples of subjects include humans, dogs, cats, cows, goats, and mice, including transgenic species The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model.

As used herein, said cavity includes, but not limit to, any of nasal cavity tumor resection, paranasal sinuses tumor resection, oral cavity tumor resection, salivary glands tumor resection, pharynx tumor resection, larynx tumor resection, and scar cavity of a melanoma resection. The bed of cheloid scars after resection could be treated by the present composition, in order to avoid cheloid or hypertrophic scar formation in the population known at risk for such reactions.

The compositions of the present invention can be used in the form of a solid, a solution, an emulsion, a dispersion, a micelle, a liposome, and the like, wherein the resulting composition contains one or more of the compounds of the present invention, as an active ingredient, in admixture with an organic or inorganic carrier or excipient suitable for enteral or parenteral applications. The active ingredient could be compounded, for example, With the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In additional auxiliary, stabilizing, thickening and coloring agents and perfumes could be used.

The compositions of the invention could be presented in a form suitable for oral use, for example, as tablets, troches, lozenges, aqueous or oily suspensions, dispersible powders or granules, emulsions, hard or soft capsules, or syrups or elixirs. Compositions intended for oral use could be prepared according to any method known to the art for the manufacture of pharmaceutical compositions and such compositions could contain one or more agents selected from the group consisting of a sweetening agent such as sucrose, lactose, or saccharin, flavoring agents such as peppermint, oil of Wintergreen or cherry, coloring agents and preserving agents in order to provide pharmaceutically elegant and palatable preparations. Tablets containing the active ingredient in admixture with non-toxic pharmaceutically acceptable excipients could also be manufactured by known methods. The excipients used could be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets could be uncoated or they could be coated by known techniques to delay disintegration and absorption in the gastrointestinal tract and thereby provide a sustained action over a longer period. For example, a time delay material such as glyceryl monostearate or glyceryl distearate could be employed. They could also be coated by the techniques described in the U.S. Pat. Nos. 4,256,108; 4,160,452; and U.S. Pat. No. 4,265,874, to form osmotic therapeutic tablets for controlled release.

In some cases, compositions for oral use could be in the form of hard gelatin capsules wherein the active ingredient is mixed with an inert solid diluent, for example, calcium carbonate, calcium phosphate or kaolin. They could also be in the form of soft gelatin capsules wherein the active ingredient is mixed with Water or an oil medium, for example, peanut oil, liquid paraffin, or olive oil.

The compositions of the invention could be presented in a form suitable for bolus injection or continuous infusion. Formulations for injection could be presented in unit dosage form e.g. in syringes, ampoules or in multi-dose containers, with an added preservative. The compositions could take such forms as suspensions, solutions or emulsions in oily or aqueous vehicles, and could contain formulatory agents such as suspending, stabilising and/or dispersing agents. Alternatively, the active ingredients could be in powder form for constitution with a suitable vehicle, e.g. sterile pyrogen-free water, before use.

EXAMPLES

The examples below are non-limiting and are merely representative of various aspects and features of the present invention.

Material and Methods

Cell Culture

Human oral squamous cell carcinoma (OSCC) cell lines, Ca922, OSC20, OECM-1, OC3, CGHNC9, HSC3, plus A549, MDA-MB-231, MCF7, Huh7, HeLa-Kyoto, Detroit 562, H520, H2170, and 293T cells were used in this study. Ca922, CGHNC9, MDA-MB-231, MCF7, Huh7, HeLa-Kyoto, Detroit 562, and 293T cells were all cultured in high-glucose Dulbecco's Modified Eagle Medium (DMEM). OSC20 and HSC3 cells were cultured in Dulbecco's Modified of Eagle's Medium/Ham's F-12 50/50 Mix (1:1). OECM-1, A549, H520, and H2170 cells were grown in RPMI-1640 medium. All culture media were supplemented with 10% fetal bovine serum (FBS) and 1% penicillin-streptomycin. OC3 cells were cultured in 1:1 DMEM/KSFM (keratinocyte serum-free medium) with supplied supplement of Bovine pituitary extract (BPE) and epidermal growth factor (EGF) followed by instruction. All the cells in this study were maintained at 37° C. in humidified atmosphere containing 5% $CO_2$.

Sequences of Synthetic Peptides

Sequences of synthetic peptides used in this study are listed in the following table:

TABLE 1

List of sequences of synthetic peptides

| | Peptide | Sequence |
|---|---|---|
| SEQ ID NO. 2 | GBP | NYRWRCKNQN |
| SEQ ID NO. 3 | $GBP_{W4R}$ | NYRRRCKNQN |
| SEQ ID NO. 4 | $GBP_{R3QW4R}$ | NYQRRCKNQN |

WST-8 [2-(2-methoxy-4-nitrophenyl)-3-(4-nitrophenyl)-5-(2,4-disulfophenyl)-2H-tetrazolium, monosodium salt] cell viability assay Cells were seeded into 96 well plate and incubated at 37° C. overnight. Endpoint measures of TMR-GBP or drugs were performed by water soluble tetrazolium salt (WST-8)-based colorimetric assay in triplicate which measures the metabolic conversion of WST-8 into formazan by mitochondrial dehydrogenases present in viable cells. The amount of formazan produced is proportional to the number of live cells and is expressed as cellular viability. When time was up, media were removed and supplemented with WST-8 cell viability reagent-contained cell culture medium (1:10) and incubated at 37° C. for 2 hours. Besides, three wells with WST-8-dissolved medium only (without cells) were reserved as a background control. Cell viability was measured at the absorbance of 450/655 nm wavelength by ELISA reader.

Annexin V Staining

Cells were seeded and incubated at 37° C. overnight, then treated with 1% $H_2O_2$ for 1 hour (as positive control), TMR and TMR-GBP 25 µM for 6 hours. Diluted 10× Binding Buffer to 1× using distilled water. Washed cells once in PBS, then once in 1× Binding Buffer. Resuspended cells in 1× Binding Buffer at $1-5\times10^6$/mL. Next, added 5 µL of fluorochrome-conjugated Annexin V to 100 µL of the cell suspension. Sample was incubated 10-15 minutes at room temperature. Afterwards, washed cells in 1× Binding Buffer and resuspend in 200 µL of 1× Binding Buffer. Analyzed by flow cytometry within 4 hours, storing at 2-8° C. in the dark.

DCFDA Cellular ROS Detection Assay

Seeded cells at $2.5\times10^4$ cells/well on a dark, clear bottom 96-well microplate and incubated in complete media with 10% FBS without phenol red. Prepared 1× Buffer by diluting 10× buffer in dd$H_2O$ and a working DCFDA solution (25 µM) by adding the appropriate volume of 20 mM DCFDA to 1× Buffer. Washed cells once in 1× Buffer and stained cells with 25 µM DCFDA for 45 minutes at 37° C. Then, washed cells once in 1× Buffer or 1×PBS. TMR-GBP, $H_2O_2$ and TBHP could be diluted in complete media with 10% FBS without phenol red. Added 100 µL/well of TMR-GBP, $H_2O_2$ (as positive control), TBHP (as positive control) and incubated for desired time period. Cells should not be washed after treatment with the TBHP or other compounds of interest. It should contain non-stained cells to determine background fluorescence. Read signal at Ex/Em: 485/535 nm by fluorescent plate reader Western Blotting Analysis Cells were harvested by trypsion or scratch and lysed in RIPA buffer (50 mM Tris-HCl, pH 7.4, 150 mM NaCl, 0.1% SDS, 0.5% Sodium deoxycholate, 1% NP-40) supplemented with 1× protease inhibitor cocktail. Sample was incubated on ice for 30 minutes and scraped every 10 minutes. Centrifuge at 13,000 rpm at 4° C. for 15 minutes, then collect supernatant for analysis. Protein concentration was determined by Bradford assay. First, 5× Bradford assay dye reagent was diluted into 1λ, and mixture with RIPA (as standard) or samples. Concentration was obtained by spectrophotometer measurement. Equal volume of 2× laemmli buffer containing β-ME was added into protein lysate for goal concentration. Protein samples were boiled at 100° C. for 15 minutes and resolved by 10% SDS-PAGE gel or 4%-15% gradient gel. Then, transfer to PVDF membrane by 100V or 110V voltage for 1 hour. First, incubate with primary antibodies at room temperature for 1 hour or at 4° C. overnight. The PVDF membrane was washed three times with 1×PBST for every 5 minutes. Second, membrane was incubated with secondary antibodies conjugated to horseradish peroxidase (HRP) (GE Healthcare) for at room temperature for 30 minutes. Antibodies concentration used in this analysis is 1:1000 dilution. Washing the membrane three times with 1×PBST for every 5 minutes, protein band was detected by modified ECL (dd$H_2O$, 100 nM Tris pH8.0, 200 µM p-coumaric acid, 1.25 mM luminal, 0.001% $H_2O_2$) with ImageQuant LAS 4000 digital imaging system.

Immunofluorescence Staining

Cells grown on coverslips were washed with 1×PBS and fixed by PTEMF buffer (20 mM PIPES pH 6.8, 0.2% Triton X-100, 10 mM EGTA, 1 mM MgCl2, and 4% formaldehyde) or 4% paraformaldehyde for 10 minutes at room temperature. Then, fixation buffer was replaced with 1×PBST and the cells were washed with 1×PBST for another 10 minutes at room temperature. Coverslips were washed with 1×PBST twice gently and incubated with primary antibodies at room temperature for 1 hour. Next, washed with PBST for three times (2, 2, 5 minutes). Afterwards, coverslips were cultured in Alex Fluor-conjugated secondary antibodies and DAPI at room temperature for 30 minutes, washed three times (2, 2, 5 minutes), rinsed with ddH2O and mounted with mounting medium. Antibodies concentration used in this analysis is 1:1000 dilution. Images were acquired with specific fluorescence wavelength by Leica DMI6000 inverted microscope equipped with HCX PL FL 100λ/NA1.40 objective and EMCCD camera. All images were analyzed by MetaMorph software.

Time-Lapse Live Cell Imaging

In order to monitor cell morphology and the stability of TMR-GBP, cells were incubated in 35 mm dish or 4 well dish at 37° C. overnight. Replaced the culture medium with $CO_2$-independent medium with supplement of 10% fetal bovine serum (FBS) and 1% penicillin-streptomycin, cells were treated with reagent (TMR, GBP, TMR-GBP) for the time according to the experiment and subjected to time-lapse live cell imaging. Cells were maintained on the microscope stage incubator at 37° C. Multiple-positional time-lapse imaging was performed using an automated Leica DMI6000 inverted microscope equipped with an HCX PL FL 20λ/NA0.4 objective and Andor Luca R EMCCD camera.

Images of cells were taken at different interval time and analyzed by MetaMorph software.

Statistical Analysis

All statistical analyses were performed using Microsoft Excel. At least 3 experiments were conducted for each protocol. The obtained results were expressed as mean±standard error of the mean (SEM). The statistical analysis was assessed by paired t test. P<0.05 was considered statistically significant.

Example 1

Rhodamine Conjugation is Essential for GBP Induced Cytotoxicity

To compare the impact of cell viability with different GBP conjugations, cells were treated with GBP, FITC-GBP, TMR, rhodamine-GBP, or TMR-GBP, then incubated for 48 hours, and followed by measured cells viability. It was observed that only with conjugation to rhodamine and its derivative TMR, GBP could induce cytotoxicity. GBP alone or in conjugation with FITC did not induce cytotoxicity (FIG. 1). These data indicate that TMR conjugation is likely essential for GBP-mediated cytotoxicity.

Example 2

TMR-GBP Induced Cytotoxicity is Light-Sensitive

Figure 2:
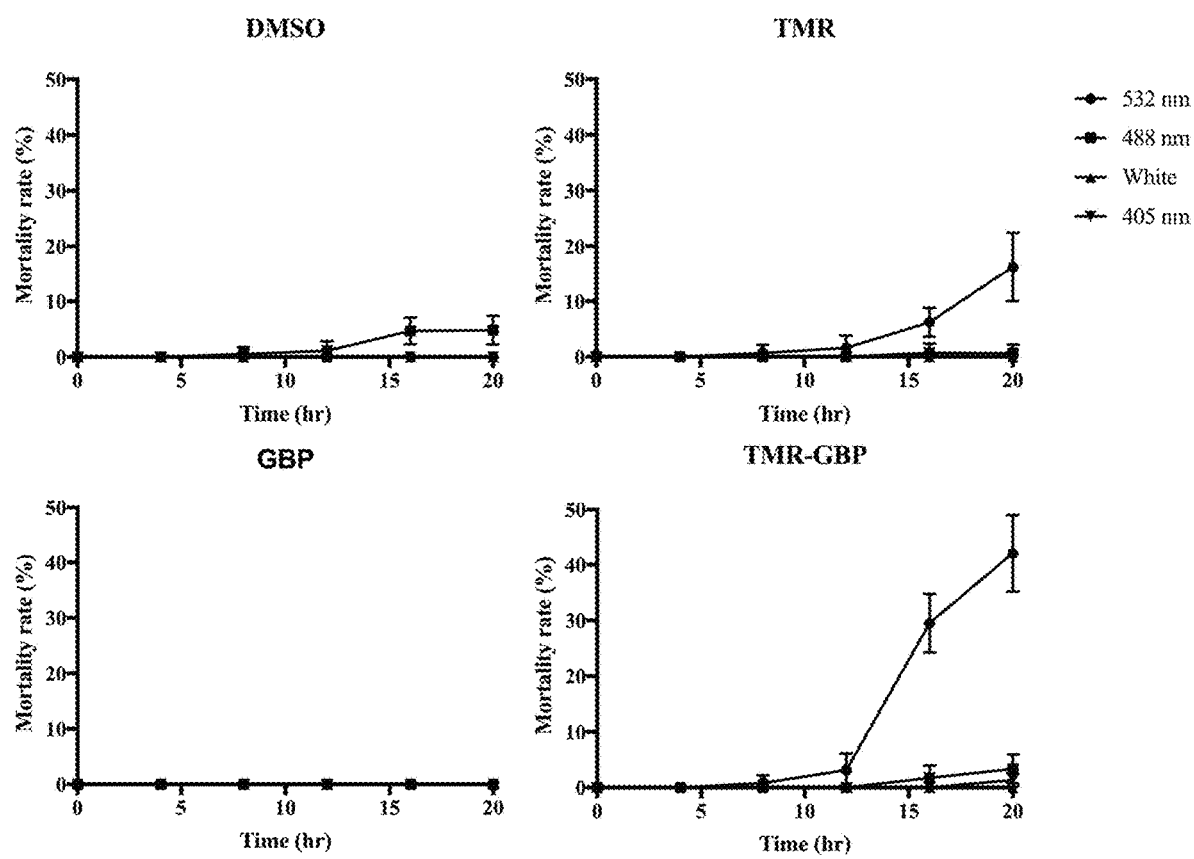
FIG. 2 shows that TMR-GBP induces cytotoxicity is light-sensitive. Ca922 cells were grown on 35 mm culture dishes overnight then treated with 1% DMSO, 12.5 μM TMR, GBP, TMR-GBP respectively and monitored by time-lapse live cell microscope. Cells were exposed to indicate wavelength once every 4 hours for 100 ms and continuously for 20 hours. At least 300 cells in five different fields were counted for each experiment using microcopy that captured images under 10× magnification. Mortality rate was evaluated by counting the percentage of dead cells in the whole population. Standard deviations of three independent experiments were indicated as bars.

To test whether light stimulation could enhance TMR-GBP induced cytotoxicity, Ca922 cells were grown on 35 mm culture dishes then treated with 1% DMSO, 12.5 µM TMR, GBP, TMR-GBP respectively. Cells were exposed to 532 nm, 488 nm, 405 nm and brightfield wavelength and monitored by time-lapse live cell microscope. After 20 hours, it is found that cells treated with DMSO or GBP were still alive under indicated wavelength light stress. In contrast, cells treated with TMR or TMR-GBP were more sensitive to 532 nm light stress and displayed cytotoxic effects (FIG. 2). These results therefore indicate that red light stress maycould increase TMR-GBP induced cytotoxicity.

Example 3

TMR-GBP Induced Cytotoxicity is Cell Type Specific

Figure 3:
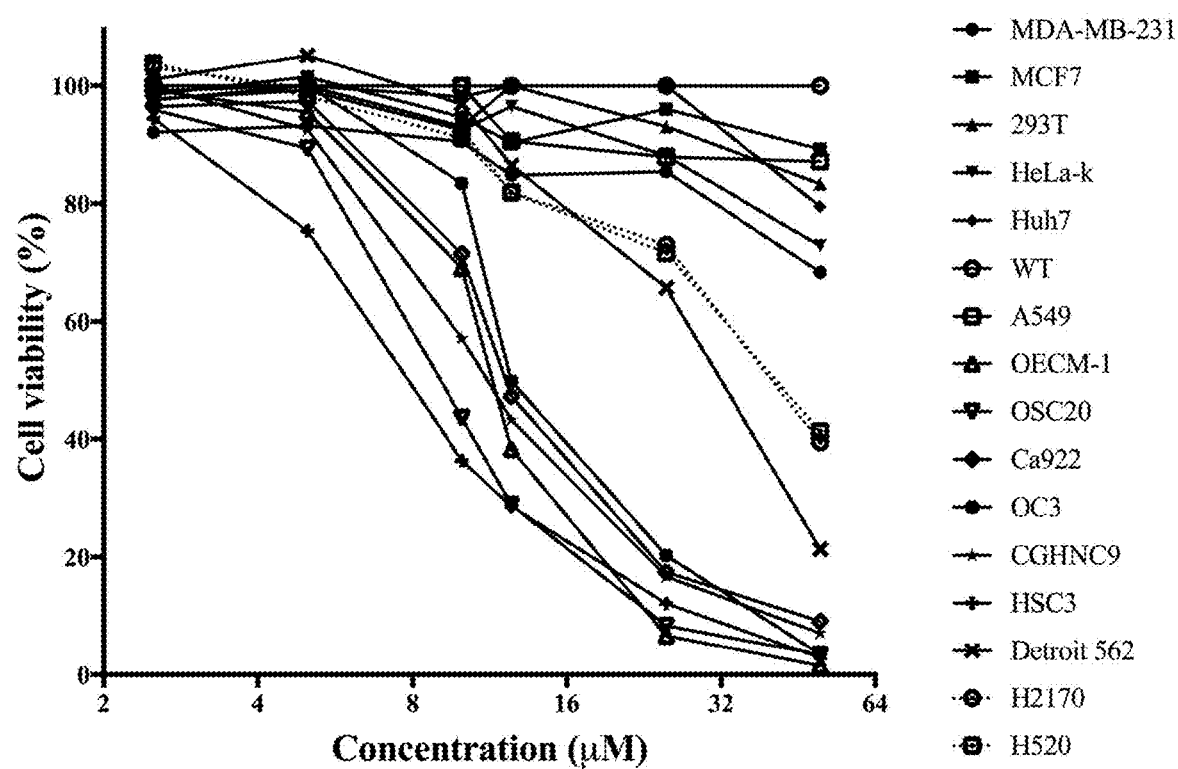
FIG. 3 shows that TMR-GBP induces cytotoxicity is cell type specific. Indicated cells were seeded in 96-well plates and then treated with TMR-GBP for 48 hours, and then subjected to WST-8 assay. Percentages of viability of indicated cells are shown.

Different cell lines, including breast cancer (MDA-MB-231, MCF7), embryonic kidney (293T), cervical cancer (HeLa-Kyoto), liver cancer (Huh7), lung cancer (A549) and oral cancer (OECM-1, OSC20, Ca922, OC3, CGHNC9, HSC3) were seeded in 96 well and exposed to different concentrations of TMR-GBP for 48 hours (FIG. 3). The effects of TMR-GBP treatment on cell viability were then assessed by WST-8 assay. 25 µM treatment significantly reduced cell viability of six oral cancer cell lines (OECM-1, OSC20, Ca922, OC3, CGHNC9, HSC3) by 80-90%. In contrast, cell viabilities of MDA-MB-231, MCF7, 293T, HeLa-Kyoto, Huh7 and A549 were not markedly affected in the presence of TMR-GBP. Accordingly, it is plausible to apply TMR-GBP as a promising cell-type specific therapeutic approach for oral cancer.

Example 4

The Effect of TMR-GBP in Different Cell Lines

Figure 4:
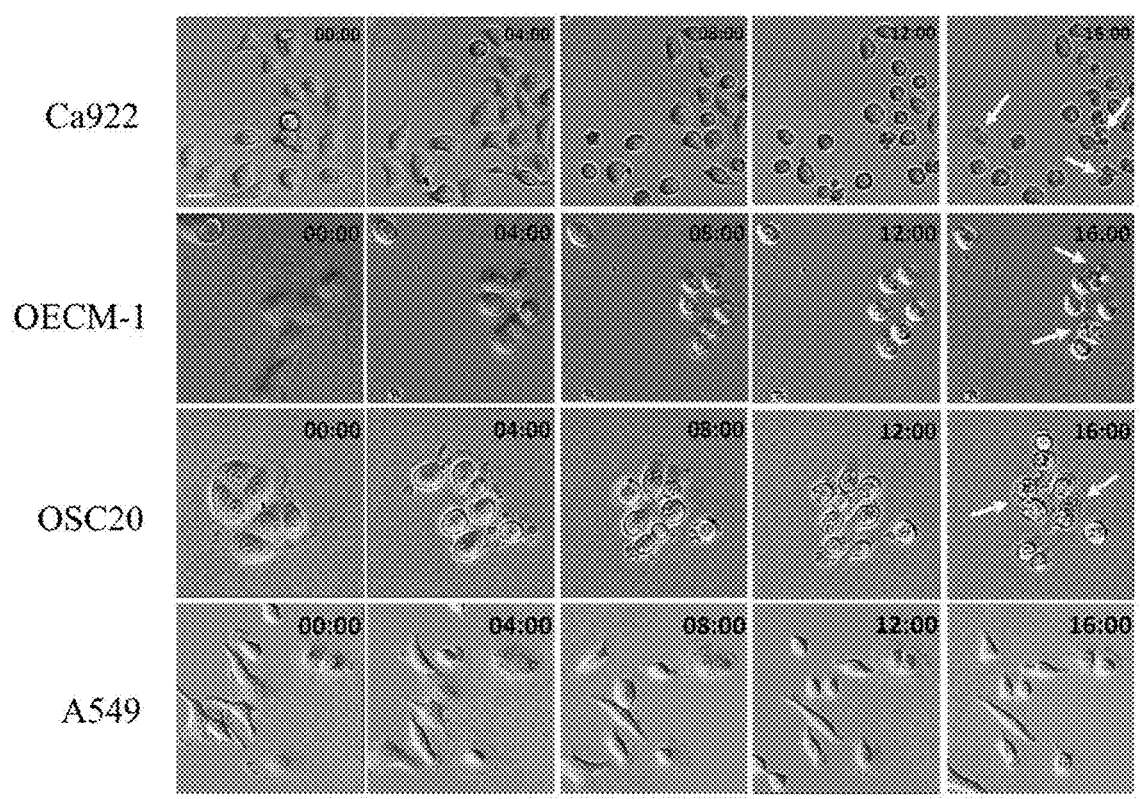
FIG. 4 shows that TMR-GBP induces cell death in oral cancer cells. Representative differential interference contrast image frames were selected to show morphology of cells under treatment with TMR-GBP. Time stamps indicate 00:00 for hr:min. The white arrows indicate dead cells. Scale bar indicates 20 μm.

To investigate the stability of GBP in cells, oral cancer cells Ca922, OECM-1, OSC20 and lung cancer cells A549 were treated with TMR-GBP and then removed unbound TMR-GBP. Next, cells were monitored by time-lapse live cell microscopy. Cells were imaged at 15 minutes interval for 16 hours. With the application of time-lapse live cell microscopy, oral cancer cells Ca922, OECM-1 and OSC20 rounded up and then most cells die in 8 hours. Conversely, lung cancer cells A549 were still alive after long-term TMR-GBP treatment (FIG. 4). These results imply that the cytotoxicity of TMR-GBP is specific to oral cancer.

Example 5

The Impact of Cell Viability with Different TMR-GBP Conjugates

Figure 5:
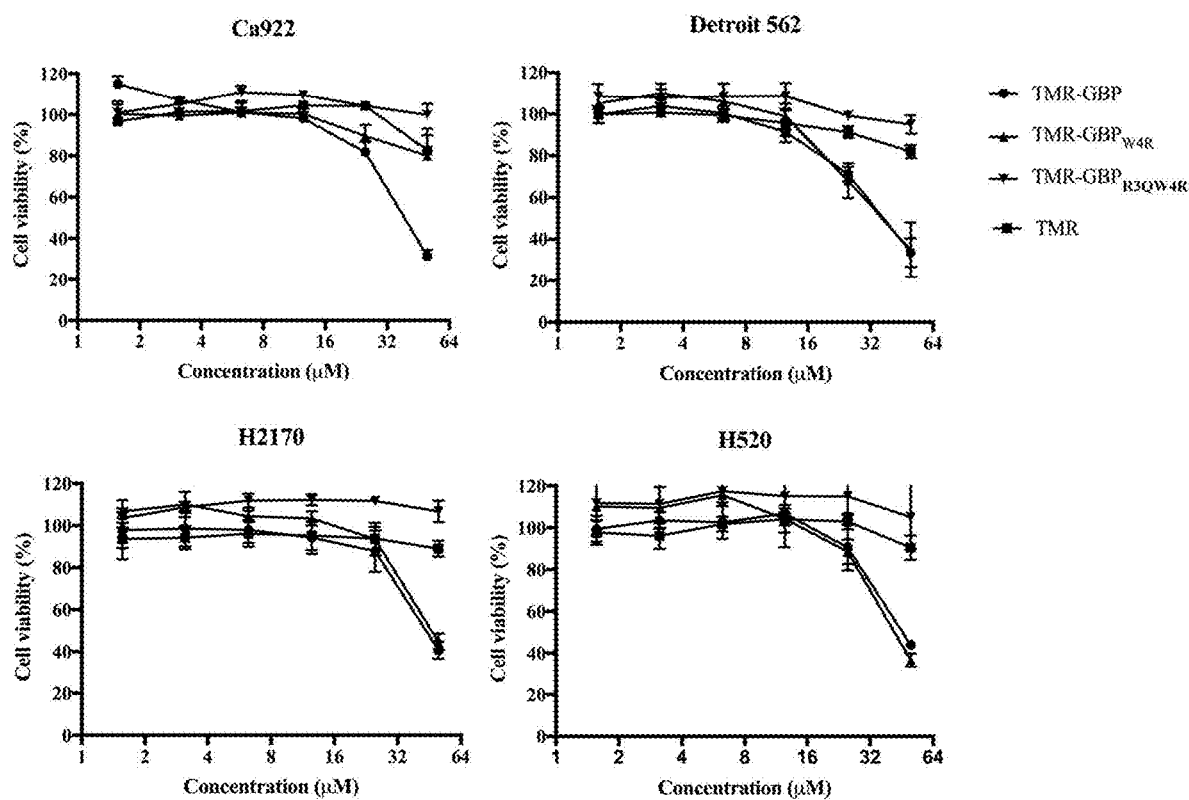
FIG. 5 shows that TMR-GBP$_{W4R}$, induces similar cytotoxic effect of TMR-GBP toward Detroit 562, H520, and H1270 but not in Ca922. Indicated cells were seeded in 96-well plates and then treated with TMR-GBP for 48 hours, and then subjected to WST-8 assay. Percentages of viability of indicated cells are shown.

To compare the impact of cell viability with different TMR-GBP conjugates, different SCC cell lines, including oral cancer (Ca922), pharynx cancer (Detroit 562), and lung cancer (H520, H2170) were seeded in 96 well and exposed to different concentrations of TMR-GBP, TMR-GBP$_{W4R}$, TMR-GBP$_{R3QW4R}$, or TMR for 48 hours. The effects of TMR-GBP conjugate treatments on cell viability were then assessed by WST-8 assay. It was observed that TMR-GBP could induce cytotoxicity in Ca922, Detroit 562, H2170, and H520. TMR-GBP$_{W4R}$ could induce cytotoxicity in Detroit 562, H2170, and H520. While neither TMR-GBP$_{R3QW4R}$ nor TMR alone induce cytotoxicity in all four cell lines (FIG. 5).

Example 6

TMR-GBP Induced Apoptosis

Figure 6A:
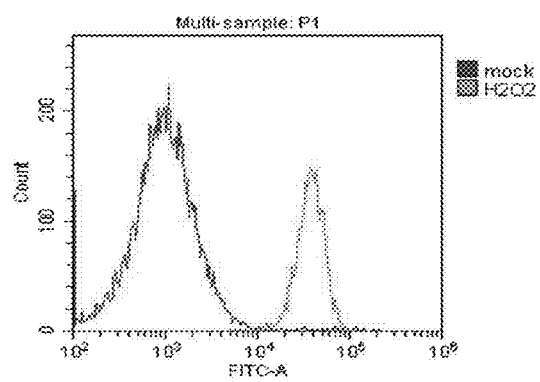
FIG. 6(A) shows that $H_2O_2$ (positive control) induces apoptosis in Ca922. Ca922 cells were treated 1% $H_2O_2$ were positively labeled with Annexin-V-FITC, followed by flow cytometry analysis. X-axis represent the fluorescent intensity, Y-axis represent cell count.
Figure 6B:
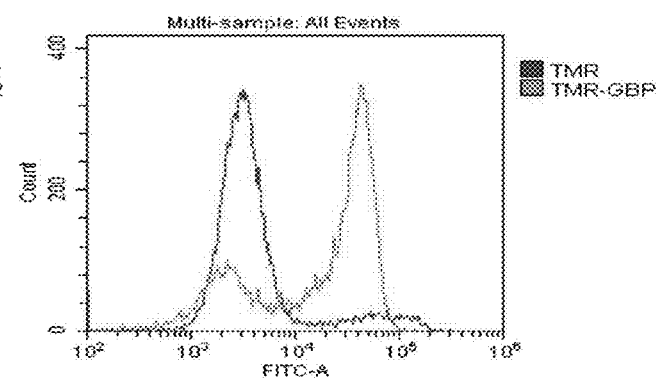
FIG. 6(B) shows that TMR-GBP induces apoptosis in Ca922. TMR-GBP triggered cells apoptosis as shown by Annexin-V-FITC staining followed by flow cytometry analysis. X-axis represent the fluorescent intensity, Y-axis represent cell count.
Figure 6C:
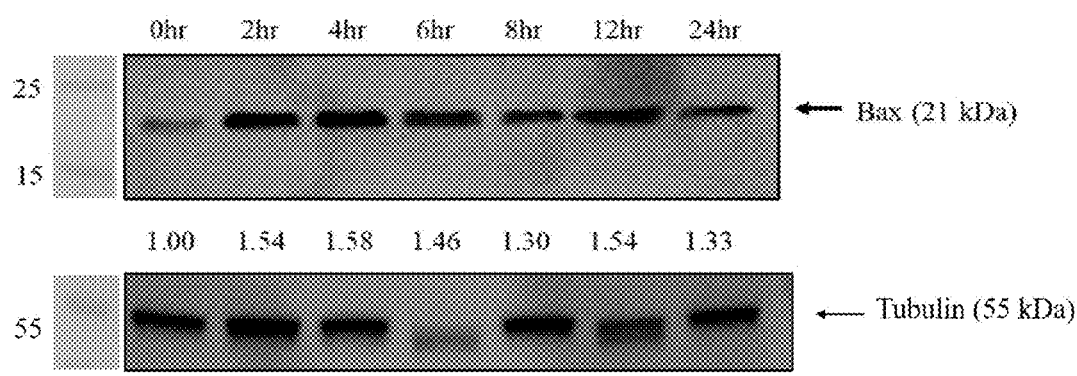
FIG. 6(C) shows that TMR-GBP induces Bax activation in Ca922 apoptosis. Protein expression of pro-apoptotic protein Bax were examined in Ca922 cells treated with 25 μM TMR-GBP for indicated time points. The relative protein level was presented below the blot as ratios which was normalized to Bax value of control cells (0 hour).

Upon initiation of apoptosis, phosphatidylserine (PS) lost its asymmetric distribution across the phospholipid bilayer and was translocated to the extracellular membrane. At this stage, PS could be detected by fluorescently labeled Annexin V. To further validate TMR-GBP trigger oral cancer cells apoptosis, Ca922 cells were treated with 1% $H_2O_2$, 12.5 µM TMR and TMR-GBP, and then stained with Annexin V-FITC. Cells with no treatment (mock) and 1% $H_2O_2$ were applied as negative and positive control, respectively (FIG. 6A). It was found that Ca922 were positively labeled by Annexin-V-FITC, indicating that TMR-GBP induced apoptosis in Ca922 (FIG. 6B). Furthermore, protein expression of pro-apoptotic protein Bcl-2-associatedx protein (Bax) was increased upon TMR-GBP treatment (FIG. 6C). These data indicated that TMR-GBP induced apoptosis in Ca922 cells.

Example 7

Figure 7:
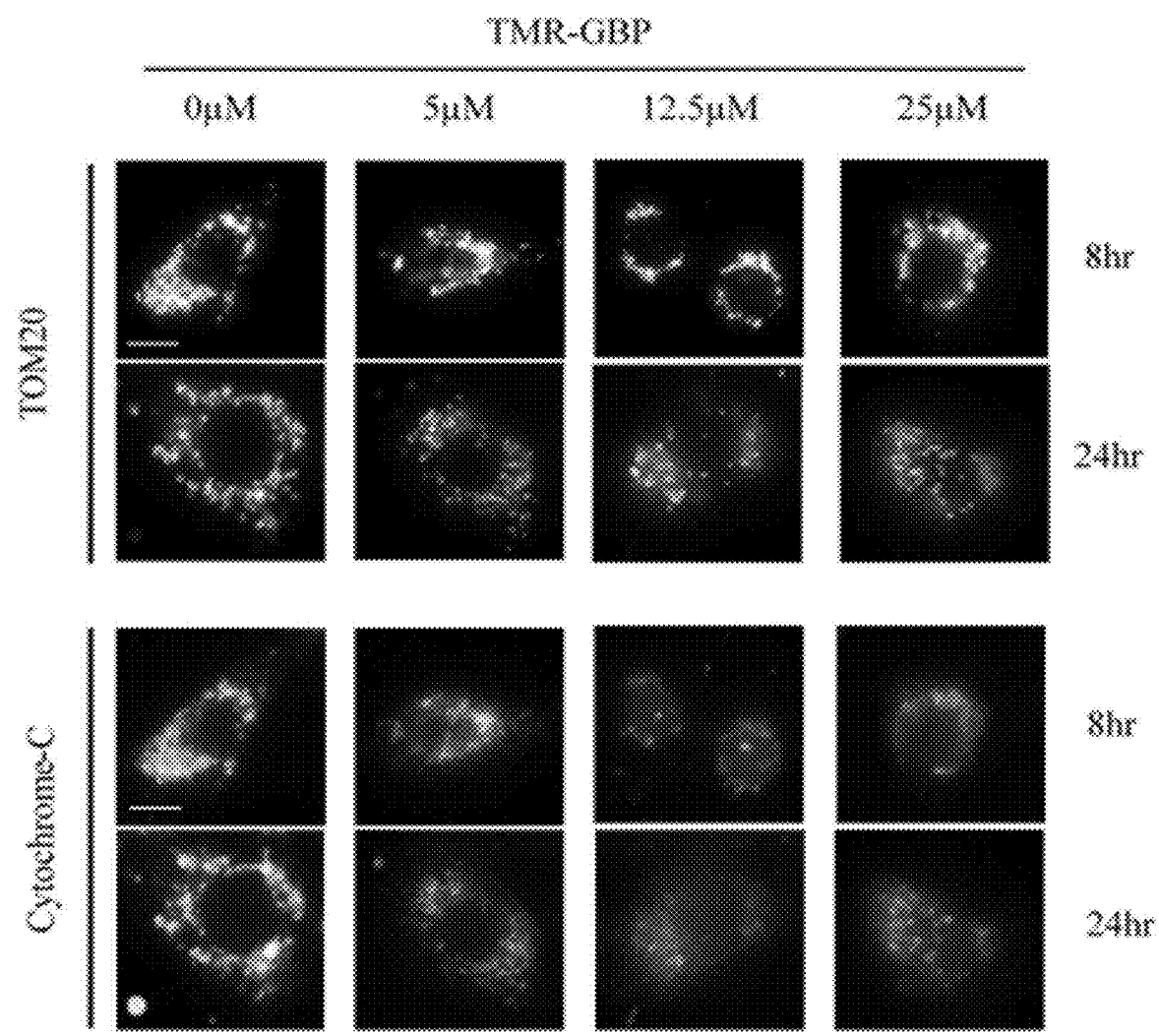
FIG. 7 shows that TMR-GBP treatment induces mitochondria fragmentation and cytochrome-c release. Ca922 cells were treated with different doses of TMR-GBP for 8 or 24 hours and then fixed with 4% formaldehyde. Representative images showing the staining of mitochondria marker TOM20 and cytochrome-c. Scale bar indicates 10 μm.

TMR-GBP Treatment Induced Mitochondria Fragmentation and Release of Cytochrome-c Whether TMR-GBP attacked mitochondria after penetrating into cells were sought to further explore. Ca922 cells were treated with different dose of TMR-GBP for 8 or 24 hours and performed immunofluorescence staining. Cells were contained with the antibodies specific to TOM20, which is a marker of mitochondria, and cytochrome-c, a small hemeprotein found loosely associated with the inner membrane of the mitochondrion. It was observed that the morphology of mitochondria became fragmented when the concentration of TMR-GBP was increased or the treatment time was extended. Cytochrome-c release upon TMR-GBP treatment was also detected (FIG. 7).

Example 8

TMR-GBP Induced Cytotoxicity is Partially Suppressed by NAC

Figure 8A:
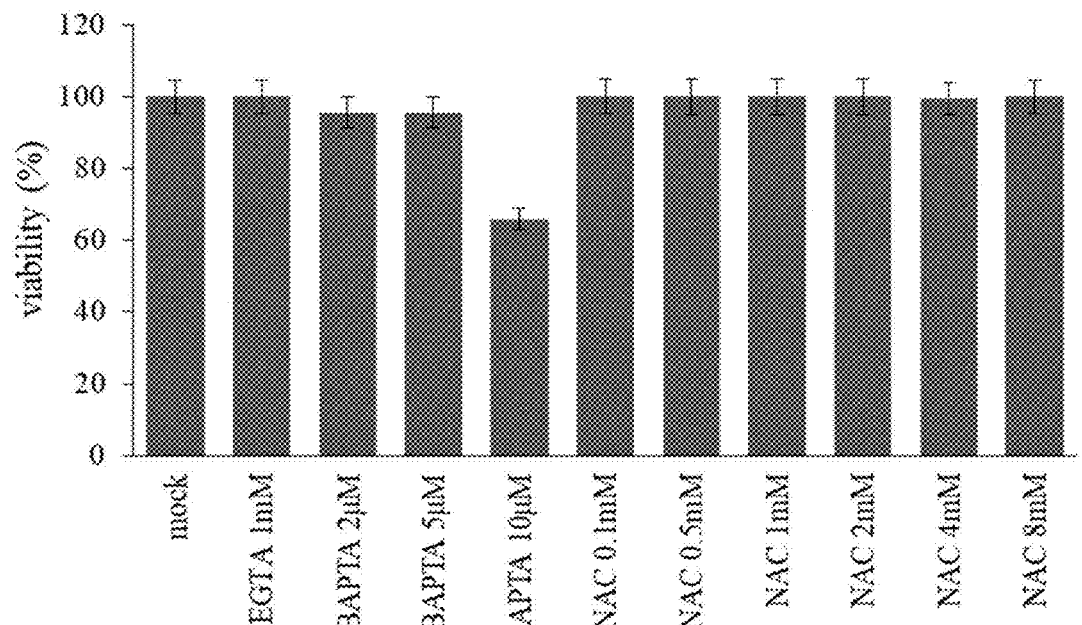
FIG. 8(A) shows that EGTA, BAPTA and NAC do not influence cell viability of Ca922 cells. Ca922 cells were seeded in 96-well plates and then pretreated with EGTA (ethylene glycol tetraacetic acid), BAPTA (1,2-bis(o-aminophenoxy)ethane-N,N,N',N'-tetraacetic acid) and N-acetyl-cysteine (NAC). Cell viability of Ca922 upon indicated treatment was evaluated by WST-8 assay. Percentages of viability of indicated cells are shown.
Figure 8B:
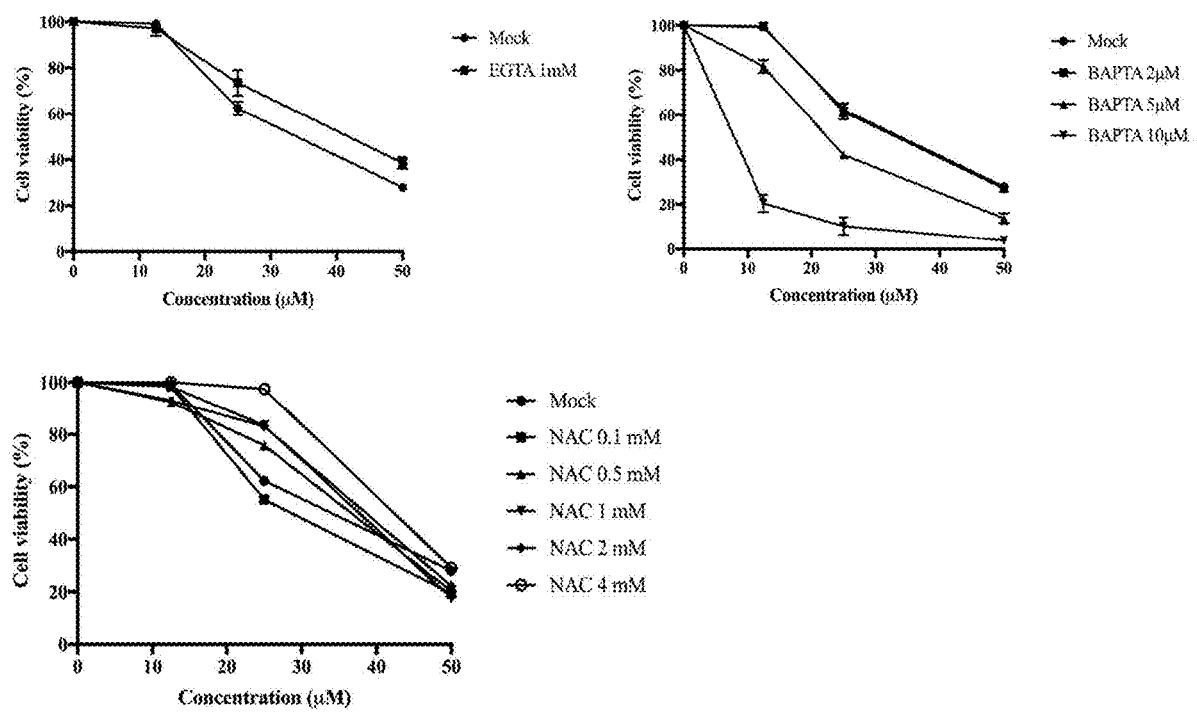
FIG. 8(B) shows that TMR-GBP induces cytotoxicity is partially suppressed by NAC. Ca922 cells were seeded in 96-well plates and then pretreated with EGTA, BAPTA and NAC for 2 hours before TMR-GBP treatment. Cell viability was measured by WST-8 assay. Ca922 cell viabilities in response to co-treatments with TMR-GBP and calcium chelator (EGTA, BAPTA-AM) or ROS scavenger NAC were shown. Standard deviations of three independent experiments were indicated as bars.

Whether mitochondria fragmentation and cell death depend on the disruption of calcium homeostasis or ROS generation was continued to investigate. First of all, Ca922 cells were exposed to different concentrations of calcium-chelators BAPTA-AM and EGTA or ROS scavenger NAC for 50 hours then measured cell viability (FIG. 8A). Cotreatments with 1 mM of EGTA, 2 µM, 5 µM of BAPTA-AM and 0.1 to 8 mM of NAC showed no significant effect on cell viability. However, 10 μM BAPTA-AM was a bit toxic to Ca922 cells. Next, cells were pretreated with BAPTA-AM, EGTA or NAC for 2 hours, followed by exposed to different concentrations of TMR-GBP (0,12.5,25 or 50 μM) for 48 hours and measured cell viability (FIG. 8B). BAPTA-AM and EGTA treatment is expected to rescue cell viability if cell death depends on the disruption of calcium homeostasis. However, TMR-GBP induced cytotoxicity was partially suppressed by NAC. These results therefore suggested that TMR-GBP induced cell death is likely depended on the presence of ROS in response to TMR-GBP.

Example 9

TMR-GBP Induced ROS Generation in Ca922 Cells

Figure 9:
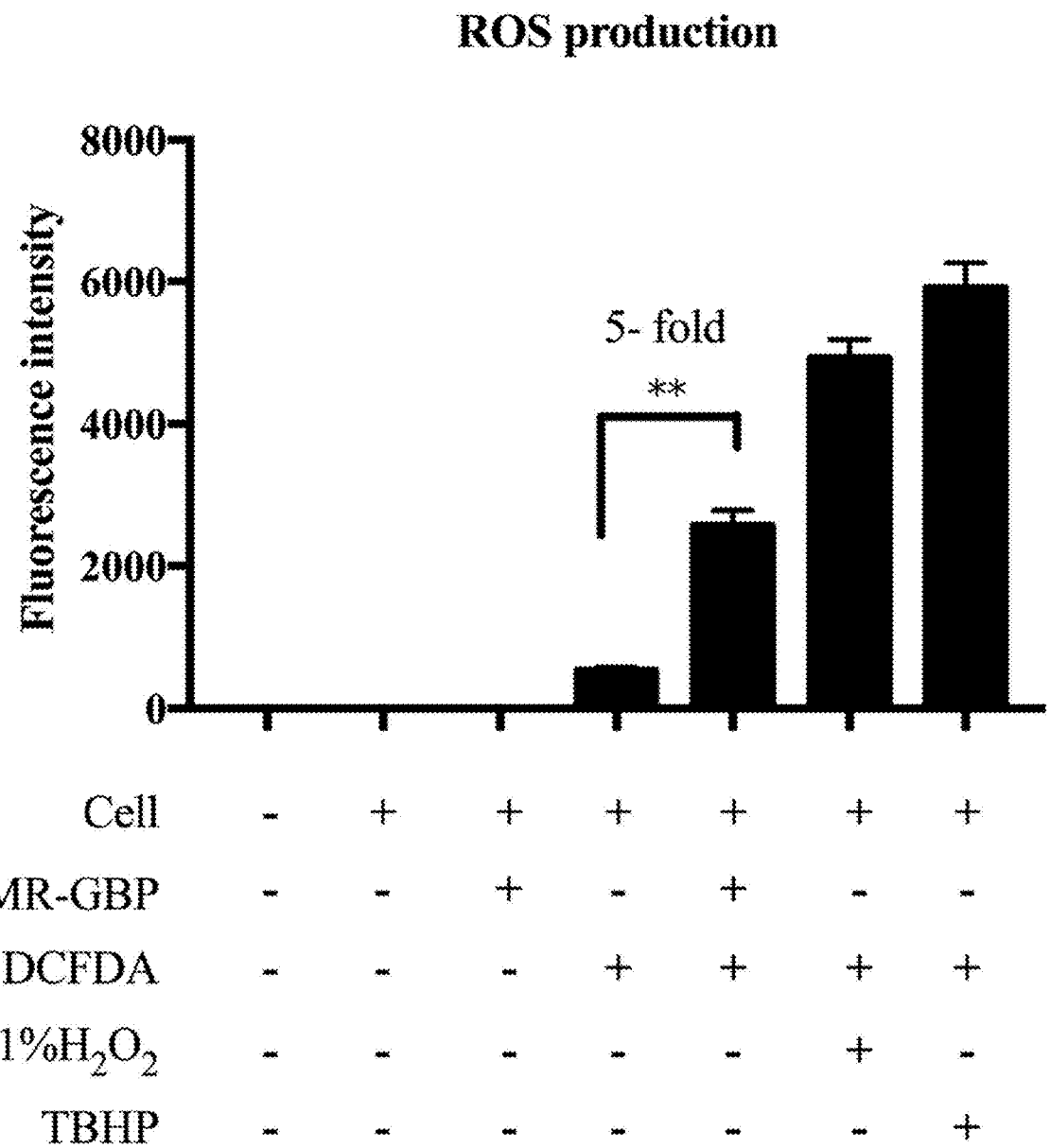
FIG. 9 shows that TMR-GBP induces ROS generation in Ca922 cells. Ca922 cells were seeded in dark, clear bottom 96-well microplate with 25,000 cells per well. Cells were then labeled with 25 μM DCFDA for 45 minutes and 25 μM TMR-GBP for 6 hours. 1% $H_2O_2$ (1 hour) and 55 mM TBHP (4 hours) treatments were positive control, mimic ROS activity to oxidize DCFDA to fluorescent DCF. Cells were then analyzed on a fluorescent plate reader. Standard deviations of three independent experiments were indicated as bars.

To further validate if TMR-GBP induced cell death depends on ROS production, ROS production was measured. Ca922 cells were seeded onto clear bottom 96-well microplate and then labeled with DCFDA in dark for the detection of intracellular ROS. After DCFDA incubation, cells were exposed to 25 μM TMR-GBP for 6 hours. Cells treated with 1% $H_2O_2$ or 55 mM TBHP treatments were applied as positive controls. After background subtraction, it was found that TMR-GBP treatment increased ROS by 5-folds when compared with control cells (FIG. 9). In the absence of DCFDA labelling, the fluorescence signal of TMR-GBP treatment was not been detected, indicating that the presence of TMR had no impact on the background readout of DCFDA. Taken together, these results were in consistent with previous assumption that TMR-GBP induced cell death was dependent on ROS generation in oral cancer cells.

Example 10

TMR-GBP Treatment Induced DNA Damage

Figure 10A:
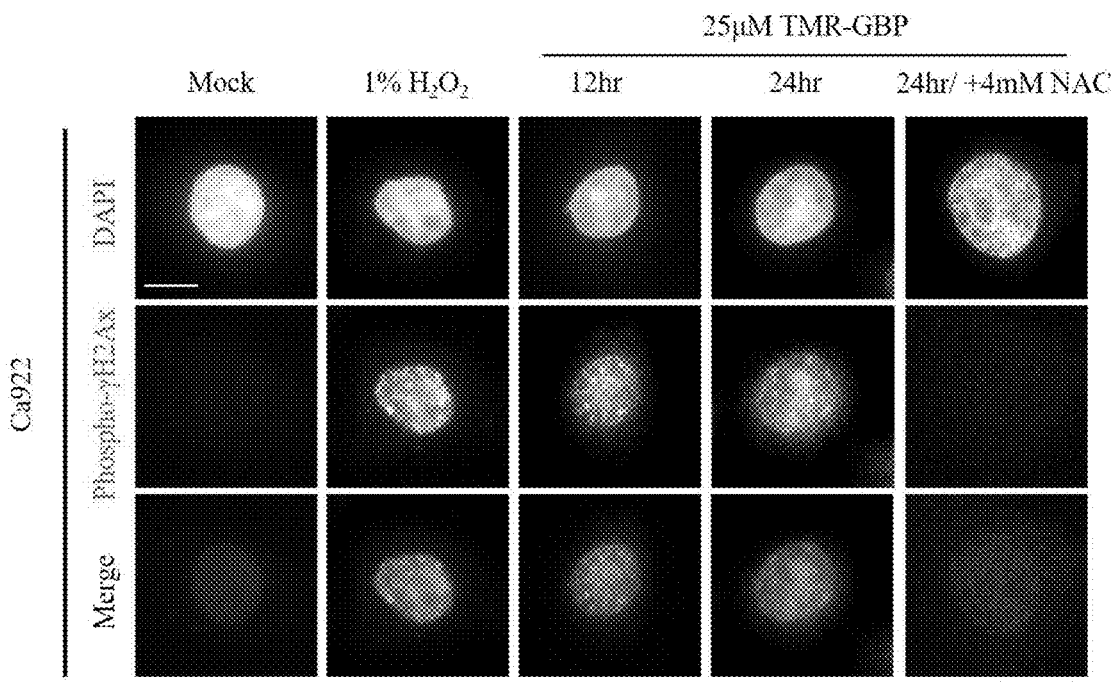
FIG. 10(A) shows that TMR-GBP treatment induces DNA damage. Representative images showing DAPI-labelled nucleus (shown in blue) co-stained with phospho-γH2Ax (green). Ca922 cells were treated with 25 μM TMR-GBP for 12 or 24 hours followed by immunofluorescence staining. Foci in the nucleus indicated damaged DNA. Scale bar indicates 10 μm.
Figure 10B:
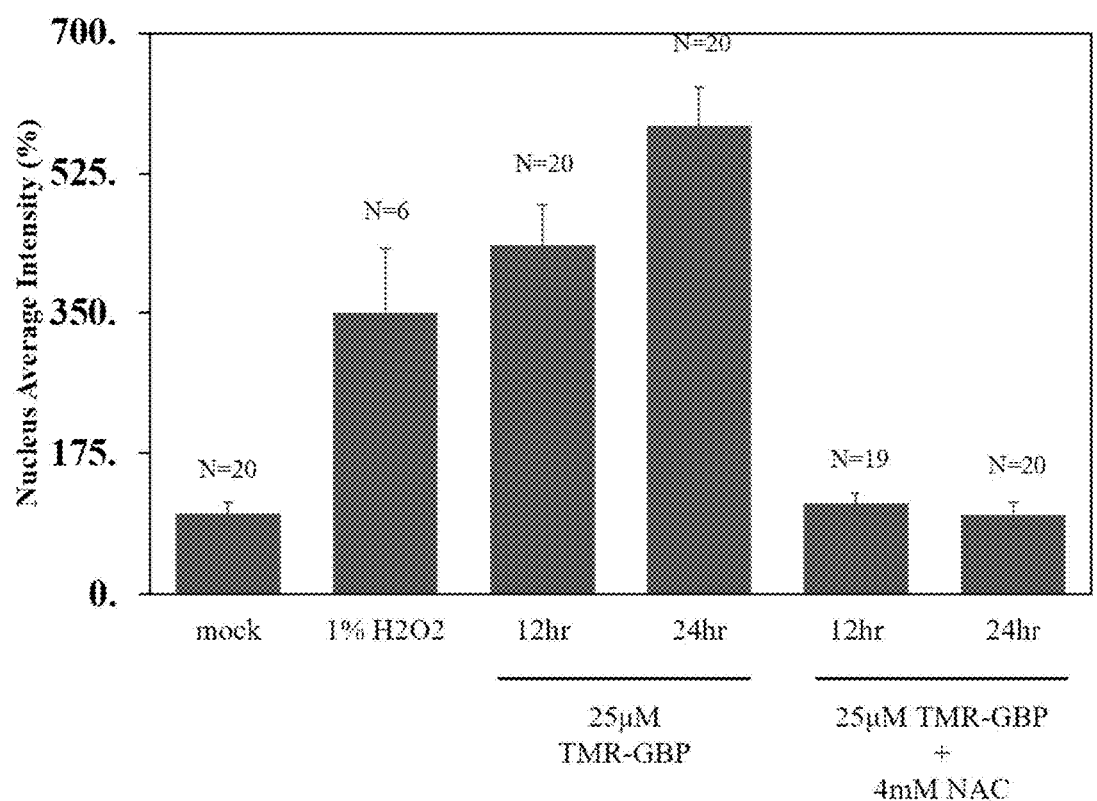
FIG. 10(B) shows that TMR-GBP treatment induces DNA damage. Bar chart showed the percentage of nucleus average intensity. At least 20 cells were counted in each category. Bars indicate standard deviations from three independent experiments.

Ca922 cells were treated with 25 μM TMR-GBP and performed immunofluorescence staining of H2Ax to investigate DNA damage. $H_2O_2$ treatment was applied as a positive control. Compared to control cells, many foci were observed accumulating in the nucleus upon $H_2O_2$ and TMR-GBP treatment. Conversely, it was hardly detected any phospho-γH2Ax signal in control cells and cells co-treated with TMR-GBP and NAC (FIG. 10A). The intensity of nuclear H2Ax was then measured and found that the intensity of γH2Ax in TMR-GBP treated cells were increased by 4-folds over control cells or cells which co-treated with TMR-GBP and NAC (FIG. 10B). Thus, TMR-GBP treatment induced DNA damage can be prevented by treatment with NAC.

Example 11

TMR-GBP Induces PARP Cleavage in a Caspase-Independent Manner.

Figure 11A:
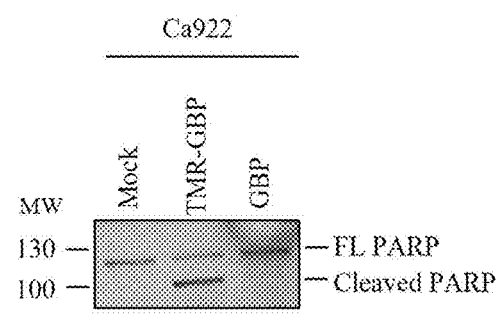
FIG. 11(A) shows that TMR-GBP induces PARP cleavage without caspase activation. Protein expression of Poly (ADP-ribose) polymerase (PARP) were examined in Ca922 cells treated with 25 μM TMR-GBP for 6 hours.

Cytotoxic effects of different type of GBP, including TMR-GBP and GBP, on Ca922 cells were tested. Previously it had been found that TMR-GBP treatment induced DNA damage in Ca922 cells (FIG. 10A, 10B). Protein expression of Poly (ADP-ribose) polymerase (PARP) involves in a number of cellular processes including DNA repair, genomic stability, and programmed cell death. Cell lysates were collected and protein expression of PARP were examined. Compared to GBP, only TMR-GBP induced PARP cleavage (FIG. 11A).

Figure 11B:
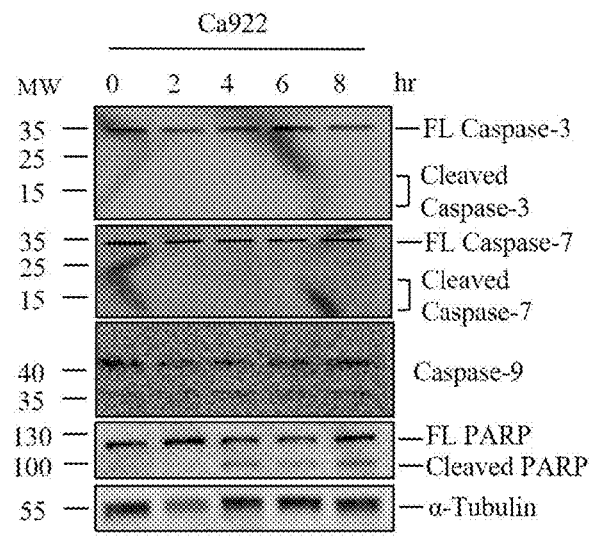
FIG. 11(B) shows that TMR-GBP induces PARP cleavage without caspase activation. Protein lysate of Ca922 cells treated with TMR-GBP 25 μM were blotted with antibodies against Caspase-3, Caspase-7, Caspase-9 and Poly (ADP-ribose) polymerase (PARP). Representative blots are shown.
Figure 11C:
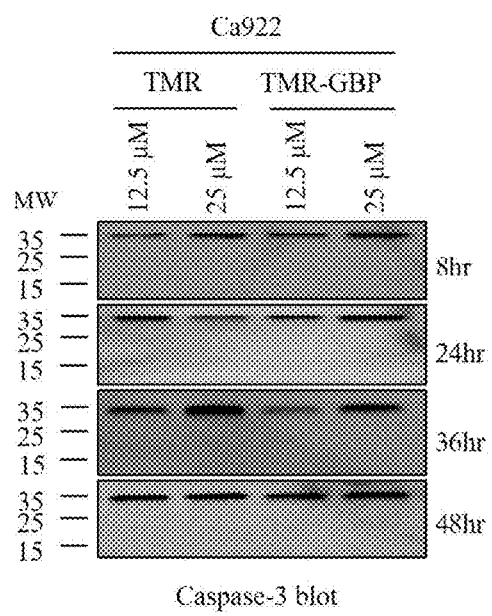
FIG. 11(C) shows that TMR-GBP induces PARP cleavage without caspase activation. Ca922 cells were treated with TMR-GBP and collected at indicated time points. Then blotted for Caspase-3 to observe whether TMR-GBP triggered Caspase-independent apoptosis pathway.
Figure 11D:
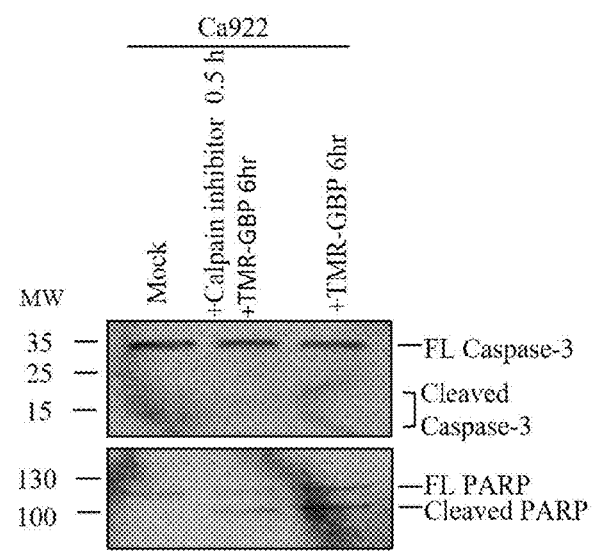
FIG. 11(D) shows that TMR-GBP induces PARP cleavage without caspase activation. Cells were pretreated with Calpain inhibitor for 30 minutes before TMR-GBP treatment and then blotted for Caspase-3.

To investigate whether TMR-GBP induced Ca922 apoptosis through caspase-dependent pathway, expressions of different caspases were examined. Interestingly, TMR-GBP treatment did not activate caspase-3, caspase-7 and caspase-9, even extended the treatment time to 48 hours (FIG. 11B, 11C). Moreover, after using calpain inhibitor to block calpain activity, TMR-GBP still induced PARP cleavage in Ca922 cells (FIG. 11D). It is therefore concluded that TMR-GBP induced cell death is independent of caspase activation.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The cells, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method of treating head and neck squamous cell carcinoma, comprising:
    administering a composition comprising a rhodamine or rhodamine derivative conjugated to a peptide comprising an amino acid sequence of SEQ ID NO: 1 to a subject suffering from head and neck squamous cell carcinoma, and
    activating the composition with light, wherein the rhodamine or the rhodamine derivative is selected from the group consisting of: Carboxytetramethylrhodamine (TAMRA), Tetramethylrhodamine (TMR) and 5/6-tetramethyl-rhodamine isothiocyanate (TRITC).

2. The method of claim 1, wherein the composition is administered into a mass of cancer cells of the head and neck squamous cell carcinoma.

3. The method of claim 1, wherein the composition induces apoptosis of the cancer cells of the head and neck squamous cell carcinoma.

4. The method of claim 3, wherein the apoptosis is independent of caspase activation.

5. The method of claim 1, wherein the composition induces mitochondria fragmentation of the cancer cells of the head and neck squamous cell carcinoma.

6. The method of claim 1, wherein the composition induces reactive oxygen species (ROS) generation of the cancer cells of the head and neck squamous cell carcinoma.

7. The method of claim 1, wherein the composition induces DNA damage of the cancer cells of the head and neck squamous cell carcinoma.

8. The method of claim 1, wherein the light is with a wavelength of 380 nm to 750 nm.

9. The method of claim 8, wherein the light is with a wavelength of 400 nm to 620 nm.

10. The method of claim 9, wherein the light is with a wavelength of 470 nm to 580 nm.

* * * * *

SEQUENCE LISTING

```
<160> NUMBER OF SEQ ID NOS: 4

<210> SEQ ID NO 1
<211> LENGTH: 10
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 1

Asn Tyr Arg Xaa Arg Cys Lys Asn Gln Asn
1               5                   10

<210> SEQ ID NO 2
<211> LENGTH: 10
<212> TYPE: PRT
<213> ORGANISM: Homo sapiens
```

```
<400> SEQUENCE: 2

Asn Tyr Arg Trp Arg Cys Lys Asn Gln Asn
1               5                   10

<210> SEQ ID NO 3
<211> LENGTH: 10
<212> TYPE: PRT
<213> ORGANISM: Homo sapiens

<400> SEQUENCE: 3

Asn Tyr Arg Arg Arg Cys Lys Asn Gln Asn
1               5                   10

<210> SEQ ID NO 4
<211> LENGTH: 10
<212> TYPE: PRT
<213> ORGANISM: Homo sapiens

<400> SEQUENCE: 4

Asn Tyr Gln Arg Arg Cys Lys Asn Gln Asn
1               5                   10
```